US00PP23155P2

(12) United States Plant Patent
Pinkham et al.

(10) Patent No.: US PP23,155 P2
(45) Date of Patent: Oct. 30, 2012

(54) ***HEMEROCALLIS* PLANT NAMED 'VT SPIRIT'**

(50) Latin Name: ***Hemerocallis* hybrid**
Varietal Denomination: VT Spirit

(75) Inventors: Linda D. Pinkham, Carrollton, VA (US); Rumen Vasilev Conev, St. Catharines (CA)

(73) Assignee: Virginia Nurserymen's Horticulture Research Foundation Inc., Christiansburg, VA (US)

( * ) Notice: Subject to any disclaimer, the term of this patent is extended or adjusted under 35 U.S.C. 154(b) by 0 days.

(21) Appl. No.: 13/134,942

(22) Filed: Jun. 21, 2011

(51) Int. Cl.
*A01H 5/00* (2006.01)

(52) U.S. Cl. ..... Plt./312

(58) Field of Classification Search ..... Plt./312
See application file for complete search history.

*Primary Examiner* — Kent L Bell
(74) *Attorney, Agent, or Firm* — Penny J. Aguirre

(57) ABSTRACT

A new cultivar of *Hemerocallis* named 'VT Spirit' that is characterized by being a triploid that does not produce seed pods, its blooming habit that commences early in the season with re-bloom for about 10 weeks, its flowers that are yellow-orange in color with a wide maroon eye zone, a yellow-orange throat, and ruffled petal margins that are maroon in color, its evergreen foliage habit, and its vigorous growth habit.

2 Drawing Sheets

Botanical classification: *Hemerocallis* hybrid.
Cultivar designation: 'VT Spirit'.

BACKGROUND OF THE INVENTION

The present invention relates to a new and distinct cultivar of *Hemerocallis* plant of hybrid origin, botanically known as *Hemerocallis* 'VT Spirit' and will be referred to hereafter by its cultivar name, 'VT Spirit'.

The new cultivar was developed through a breeding program conducted by the Inventors in Danville, Va., and Carrollton, Va. The objective of the breeding program was to develop new cultivars of triploid *Hemerocallis* by crossing diploid and tetraploid cultivars of *Hemerocallis*. The goal of the breeding program was to create new cultivars of *Hemerocallis* that are sterile, long blooming, and attractive.

'VT Spirit' arose from a cross made in the summer of 2005 between 'Pumpkin Prince' (not patented) as the female parent and 'Pumpkin Kid' (not patented) as the male parent. Seed pods were collected when they were 12 days old and sent overnight to the lab in Danville, Va., where embryo rescue was performed. The resulting plants were lined out for evaluation in Carrollton, Va., in the spring of 2006. 'VT Spirit' was selected as a single unique plant in May of 2007.

Asexual reproduction of the new cultivar was first accomplished by division by one of the Inventors in Danville, Va. in 2007. Propagation by division and tissue culture has determined that the characteristics of this cultivar are stable and are reproduced true to type in successive generations.

SUMMARY OF THE INVENTION

The following traits have been repeatedly observed and represent the characteristics of 'VT Spirit'. These attributes in combination distinguish 'VT Spirit' as a new and distinct cultivar of *Hemerocallis*.

1. 'VT Spirit' is a sterile triploid and does not produce seed pods.

2. 'VT Spirit' commences blooming early in the season and is long blooming; re-blooming for about 10 weeks.
3. 'VT Spirit' exhibits a very vigorous growth habit.
4. 'VT Spirit' exhibits flowers that are yellow-orange in color with a wide maroon eye zone, a yellow-orange throat, and ruffled petal margins that are maroon in color.
5. 'VT Spirit' has an evergreen foliage habit.

The female parent, 'Pumpkin Prince', differs from 'VT Spirit' in being a tetraploid, in having a shorter scape, and in having a shorter blooming period. The male parent, 'Pumpkin Kid' differs from 'VT Spirit' in being a diploid, in having a shorter scape, in having a shorter blooming period, and in having flowers that are less intense in color with petal margins that are not as ruffled. 'VT Spirit' can be most closely compared to the cultivars 'Mary's Gold' (not patented) and 'Ed Murray' (not patented). Both are similar to 'VT Spirit' in being triploids. 'Mary's Gold' differs from 'VT Spirit' in lacking a re-blooming habit, in having a dormant foliage habit and in having flowers that lack eye zones, petal margin coloration, and ruffles on the petal margins. 'Ed Murray' differs from 'VT Spirit' in lacking a re-blooming habit and in having smaller flowers that lack eye zones, petal margin coloration, and ruffles on the petal margins.

BRIEF DESCRIPTION OF THE DRAWING

The accompanying colored photograph illustrates the overall appearance and distinct characteristics of the new *Hemerocallis*. The photographs were taken in early spring of a one year-old plant of 'VT Spirit' as grown outdoors in a garden from a single fan in Carrollton, Va.

The photograph in FIG. 1 provides a front view of a plant of 'VT Spirit' in bloom.

Figure 1:
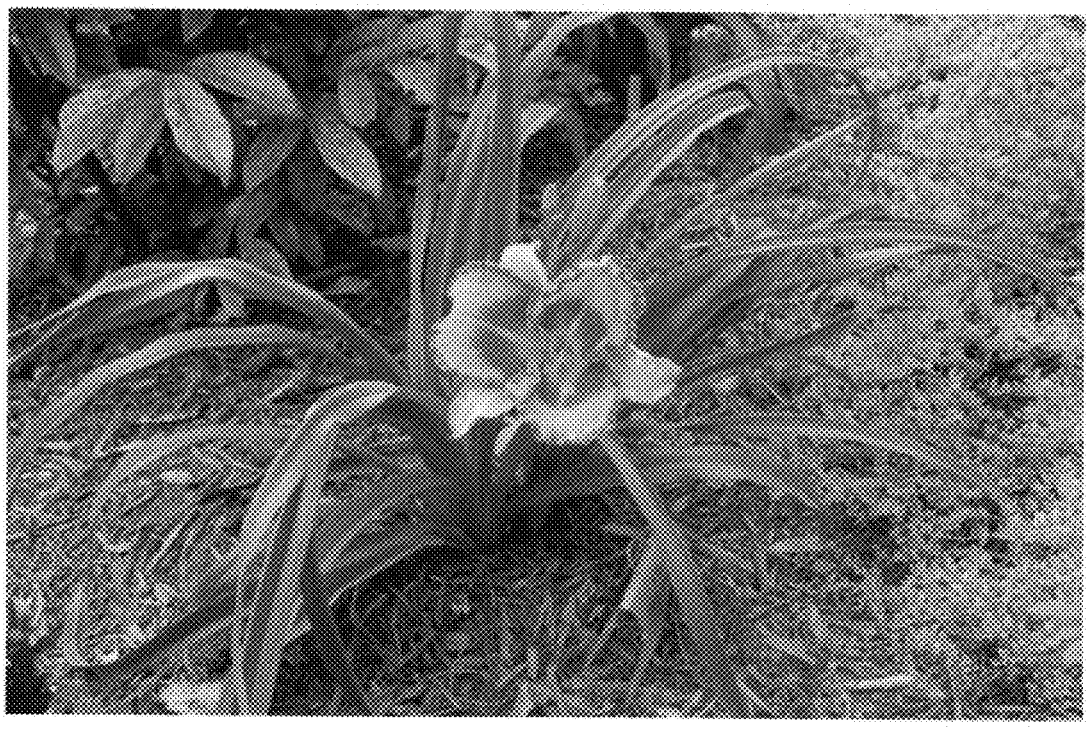
Figure 2:
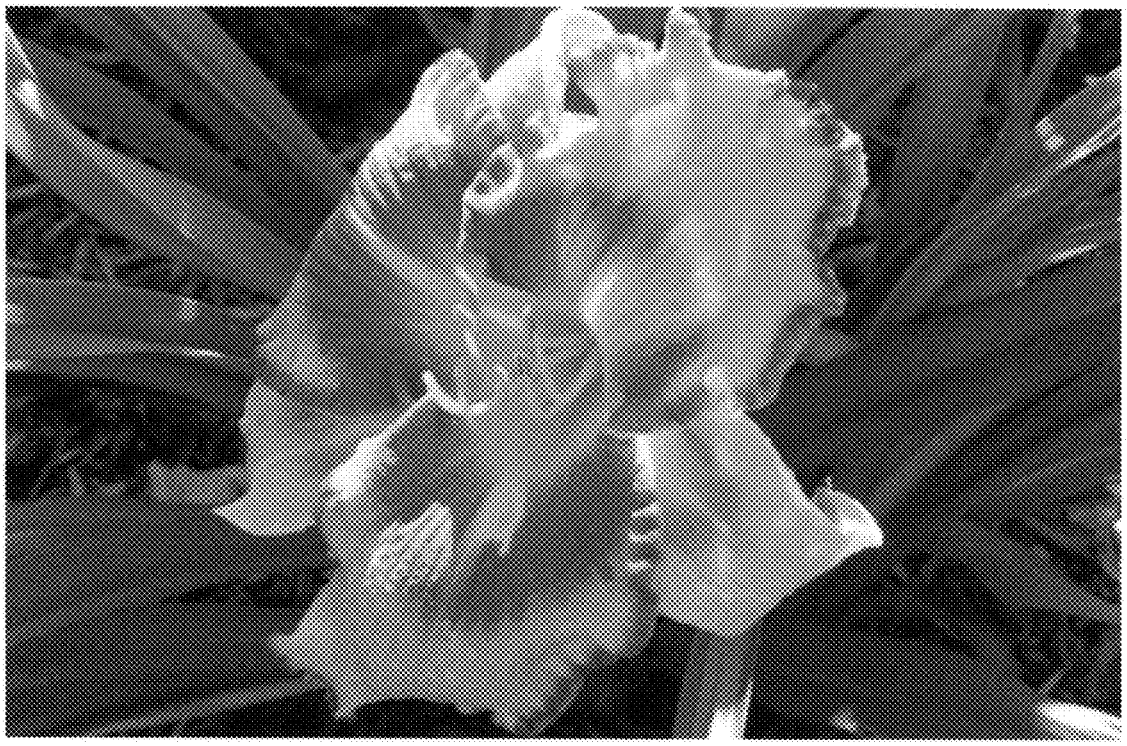

The photograph in FIG. 2 provides a close-up view of a flower of 'VT Spirit'.

The colors in the photograph may differ slightly from the color values cited in the detailed botanical description, which accurately describe the colors of the new *Hemerocallis*.

DETAILED BOTANICAL DESCRIPTION OF THE PLANT

The following is a detailed description of a one year-old plant of the new cultivar as grown in a 3-gallon container in a greenhouse in Danville, Va. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—Commencing late May in eastern Virginia and early June in western Virginia, re-blooms for about 10 weeks in Blacksburg, Norfolk and Carrollton, Va.

*Plant habit.*—Herbaceous perennial, evergreen foliage habit.

*Height and spread.*—Reaches about 58 cm in height and 45 to 60 cm in spread (in 2 to 3 years), flower scapes reaches about 58.4 cm in height.

*Hardiness.*—At least in U.S.D.A. Zones 6 to 10.

*Diseases and pests.*—No leaf streak has been observed.

*Root description.*—Fibrous roots.

*Propagation.*—Division and tissue culture.

*Growth rate.*—Vigorous and fast growing, 5 to 8 fans per season.

Foliage description:

*Leaf shape.*—Linear-broadly lanceolate.

*Leaf division.*—Simple.

*Leaf base.*—Sheathed to crown.

*Leaf apex.*—Narrowly acute.

*Leaf venation.*—Longitudinal, parallel, not prominent, same color as leaves.

*Leaf margins.*—Entire.

*Leaf attachment*.—Sheathed, not petiolate.

*Leaf arrangement.*—Equitant, fan-shaped.

*Leaf orientation.*—Held upright and upper one third slightly pendulant once matured.

*Leaf surface.*—Glabrous.

*Leaf color.*—Young and mature leaves (upper and lower surface); a blend of 138A and 144A.

*Leaf size.*—Up to 50.8 cm in length, an average of 3.2 cm in width.

*Leaf quantity.*—About 19 leaves per fan.

Flower scape description:

*Scape shape.*—Oval, pithy.

*Scape number.*—1 per fan.

*Scape aspect.*—Straight, held upright.

*Scape size.*—Up to 58.4 cm in length and 0.95 cm in width.

*Scape color.*—138A.

*Scape surface.*—Glabrous, satiny.

*Scape branching.*—An average 3 branches.

*Scape leaves.*—An average of 6 per scape (including petiole leaves), a blend of 1378A, 144A and 144B in color, turning to a blend of 144A and 137C, 2 cm to 17 cm in length, 8 mm to 1.3 cm in width, lanceolate in shape, sheathed base, acuminate apex, margin entire and 138D in color, glabrous surface.

Flower description:

*Inflorescence type.*—Scape bearing an average of 15 single flowers, one or more flowers are open at a time.

*Inflorescence size.*—Varies with opening of flowers, an average of 13 cm in width and 8 cm in depth — per branch.

*Lastingness of flowers.*—About 24 hours, self cleaning.

*Flower size.*—An average of 13 cm in diameter and 7.6 cm in depth (excluding pistil).

*Flower fragrance.*—None.

*Flower number.*—An average of 15 per scape (5 flowers per raceme).

*Flower aspect.*—Upright to slightly outward.

*Flower bud.*—Lanceolate in shape becoming more oblong close to opening, acuminate apex, an average of 6.5 cm in length and 1.5 cm in width, color; blend of 11A and 144B, 144A at very tip, seams (visible petal portion) 173D.

*Flower attachment.*—Petiolate.

*Petal number.*—3.

*Petal shape.*—Elliptic.

*Petal color.*—Upper surface; a color between 21A and 21B with a mid rib of 21D, eyezone (about 1 cm in width) and margins 59A, lower surface; 21C, throat (not distinct); a color between 21A and 21B and slight blush of 144C.

*Petal surface.*—Glabrous on upper surface, glabrous and satiny on lower surface.

*Petal margins.*—Slightly crenate, ruffled and wavy.

*Petal apex.*—Broadly acute.

*Petal base.*—Cuneate to tube portion.

*Petal size.*—Average of 7.6 cm in length to tube and 4.4 cm in width.

*Petal aspect.*—Horizontal and slightly recurved at apex.

*Sepal number.*—3.

*Sepal shape.*—Oblanceolate with an extended (2 mm in length) acuminate apical portion.

*Sepal margin.*—Entire, margins of apical portion is inward on upper surface.

*Sepal size.*—Average of 6.4 cm in length and 2.2 cm in width.

*Sepal aspect.*—Almost horizontal with apical portion slightly recurved.

*Sepal surface.*—Glabrous on upper surface, glabrous and satiny on lower surface.

*Sepal apex.*—Acuminate with apical 3 mm fused (concentric).

*Sepal base.*—Fused, cuneate to tube portion.

*Sepal color.*—Upper surface; a bend of 20A and 20B and suffused with 144C near base, apex a blend of 144C and 144D and very tip 144B, lower surface; 20A and suffused with 144C near base, apex a blend of 144B and 144C and very tip 144A.

*Tube portion.*—A blend of a blend of 145A and 145B, 8 mm in length and 6 mm in width, satiny surface.

*Peduncles.*—An average of 2.5 cm in length and 3 mm in width, oval in shape, strong, color a blend of 144A and 138A, held upright.

*Pedicels.*—An average of 5 mm in length and 3 mm in width, oval in shape, strong, color a blend of 144A and 138A, held upright.

Reproductive organs:

*Gynoecium.*—Pistil; 1, about 6.1 cm in length, style; 5.6 cm in length, 1.5 mm in width color 21C, stigmas; minute, 21D in color, ovary; conical in shape, 5 mm in length and 4.5 mm in width, 144C in color.

*Androcoecium.*—Stamens; 6, anthers; oblong in shape, 5 mm in length and 1.5 mm in width, 200A in color; filaments; 3.7 cm in length, 1.5 mm in width, 21B in color, pollen; 21A in color, moderate in quantity, not viable.

*Fruit/seeds.*—Sterile, seed pods do not develop.

It is claimed:

1. A new and distinct cultivar of *Hemerocallis* plant named 'VT Spirit' as herein illustrated and described.

* * * * *